(12) United States Patent
Van Lith

(10) Patent No.: US 11,839,217 B2
(45) Date of Patent: Dec. 12, 2023

(54) COMPOSITION COMPRISING A BIOACTIVE MOLECULE

(71) Applicant: EUCARYO BEHEER B.V., Nijmegen (NL)

(72) Inventor: Wilhelmus Antonius Maria Van Lith, Nijmegen (NL)

(73) Assignee: EUCARYO BEHEER B.V., Nijmegen (NL)

( * ) Notice: Subject to any disclaimer, the term of this patent is extended or adjusted under 35 U.S.C. 154(b) by 5 days.

(21) Appl. No.: 16/337,606

(22) PCT Filed: Sep. 28, 2017

(86) PCT No.: PCT/EP2017/074606
§ 371 (c)(1),
(2) Date: Mar. 28, 2019

(87) PCT Pub. No.: WO2018/060321
PCT Pub. Date: Apr. 5, 2018

(65) Prior Publication Data
US 2020/0029568 A1    Jan. 30, 2020

(30) Foreign Application Priority Data
Sep. 28, 2016  (NL) ...................................... 2017545

(51) Int. Cl.
A01N 43/92        (2006.01)
A01N 25/02        (2006.01)

(52) U.S. Cl.
CPC .............. A01N 43/92 (2013.01); A01N 25/02 (2013.01)

(58) Field of Classification Search
None
See application file for complete search history.

(56) References Cited

U.S. PATENT DOCUMENTS

| | | | | |
|---|---|---|---|---|
| 3,892,850 | A * | 7/1975 | Struyk | C12P 19/626 |
| | | | | 435/76 |
| 2003/0129225 | A1 * | 7/2003 | Andersson | A01N 43/90 |
| | | | | 424/450 |
| 2005/0042341 | A1 | 2/2005 | Thomas et al. | |
| 2006/0241061 | A1 * | 10/2006 | Stark | A01N 43/90 |
| | | | | 514/28 |

FOREIGN PATENT DOCUMENTS

| | | | |
|---|---|---|---|
| CN | 1854120 A | 11/2006 | |
| CN | 10742581 A | 10/2012 | |
| CN | 102742581 A * | 10/2012 | |
| WO | WO-2004105491 A1 * | 12/2004 | ............. A01N 43/90 |
| WO | 2006045831 A1 | 5/2006 | |
| WO | 2011133482 A1 | 10/2011 | |
| WO | 2012113830 A1 | 8/2012 | |

OTHER PUBLICATIONS

Anderson et al. J. of Pharm. Sci. 1985, 74(8), 815-820 (Year: 1985).*
Murti "On the preparation and characterization of water-soluble choline salts of carboxylic acid drugs" dissertation, UMKC. (Year: 1993).*
Miranda, et al. Brazilian Journal of Pharm. Sci. 2011, 47(4), 665-681. (Year: 2011).*
Gan (Food Product Design, 2010, 20(6) p. 1-4).*
Wu, T.-Y., et al. "Effect of temperature on the physico-chemical properties . . . " Int. J. Mol. Sci., 2011, 12, 2598-2617.*
Mattia, A. et al., Natamycin (Pimaricin) Safety evaluation of certain food additives . . . , prepared by Fifty seventh meeting of Joint FAO-WHO Expert Committee, Series 48, Jan. 1, 2002, pp. 49-72, vol. 48, XP055427159, Rome, Italy.
Brik, H., "Natamycin", Analytical Profiles of Drug Substances, Jan. 1, 1981, pp. 513-561, vol. 10, Academic Press, XP009017711.
Maheshwari, R., ""Mixed-solvency approach"—Boon for solubilization of poorly water-soluble drugs", Asian Journal of Pharm., Jan. 1, 2010, pp. 60-63, vol. 4, No. 1, XP055428665.
Serajuddin et al, "Salt formation to improve drug solubility", Advanced Drug Delivery Reviews, Aug. 24, 2007, pp. 603-616, vol. 59, No. 7, Elsevier, Amsterdam, NL, XP022211982.
Chinese Office Action dated Jan. 6, 2021 for family member Application No. 201780071750.X.

* cited by examiner

Primary Examiner — Erin E Hirt
(74) Attorney, Agent, or Firm — Hudak, Shunk & Farine Co. LPA

(57) ABSTRACT

A process for preparing a composition including a bioactive molecule including the steps of
  a. Dissolving a bioactive molecule having at least one acid group with a base at pH=>11 to obtain a solution A
  b. Neutralizing the solution A with an acid to obtain the composition including the bioactive molecule having a pH between 6 and 9,
wherein PEG is added before the neutralizing step in case either the base and/or the acid is an inorganic compound, and to a composition including a high concentration of natamycin.

15 Claims, 1 Drawing Sheet

COMPOSITION COMPRISING A BIOACTIVE MOLECULE

FIELD OF THE INVENTION

The invention relates to a method for preparing a water containing composition comprising a bioactive molecule comprising an acid functionality, to a composition obtainable with such method, to a composition comprising the bioactive molecule and to the use of such compositions.

BACKGROUND OF THE INVENTION

Bioactive molecules having an acid functionality are known in the art. Such molecules in general have poor solubility in water, but show activity against fungi, bacteria, may have anticancer activity or may be a plant hormone. Some of these compounds may have a ring structure, comprising a number of conjugated double bonds, hydroxyl groups and a mycosamine group; examples of such compounds are natamycin, amphotericin B, Nystatin and Filipin. Examples of plant hormones are Giberrellic acid (GA3, GA4, GA7); other compounds are Auxin (indole-3-acetic acid), Indole-3-butyric acid—Abcissic acid (S-ABA) and betulinic acid. All components have in common that they have at least one carboxylic acid group and show bioactivity, and low solubility in water, for example less than 100 mg/l water.

One particular example of a bioactive molecule is Natamycin, also known as pimaricin, which is an effective anti-fungal agent. It exerts a wide range of in vitro activity against molds and yeast, particularly of the *Candida, Aspergillus, Penicillium, Cephalosporium* and *Fusarium* species. After its isolation in 1955, it has found widespread application in the preservation of foods, in particular bakery products, meat products, beverages and dairy products (in particular cheese). Natamycin appears to possess a broader spectrum of activity than many other fungicides allowed for food application.

Despite the potential of natamycin for combatting fungi, its use in clinical medicine is still limited. This is mainly due to the low solubility of natamycin in various solvents, both aqueous and organic, that are compatible for human administration. For example, the solubility in water is 30-50 mg $L^{-1}$, and in ethanol it is 0.04-1.2 g $L^{-1}$; only the dissolved fraction has antifungal activity. In conventional natamycin-based pharmaceutical formulations, such as creams for topical treatments of skin infections, the natamycin is present in a predominantly insoluble crystalline form, leading to a low bioavailability of active natamycin. Attempts to increase the amount of dissolved natamycin in topical formulations often gave a small increase of dissolved natamycin and an antifungal activity that was still insufficient for many applications. Other attempts indeed resulted in significantly higher amounts of dissolved natamycin, but such formulations had the disadvantage that the antifungal activity had not increased accordingly (or had even decreased), or that the presence of undesired solubilizers was required. An incidental successful medical application of natamycin is in the treatment of corneal fungal infections, and the prevention of such infections in contact-lens users. However, these formulations are suspensions wherein the amount of soluble and biologically active natamycin is very small.

It is generally known that natamycin can be dissolved in an aqueous solvent with a high pH. Such procedure can be used to purify natamycin. In patent CN102742581 this procedure is used to efficiently contact dissolved natamycin with hydroxypropyl β-cyclodextrin to produce a natamycin-cyclodextrin complex. It is known in the art that inclusion complexes/compounds with natamycin can be produced using different types of cyclodextrin (β-cyclodextrin (β-CD), hydroxypropyl β-cyclodextrin (HP β-CD), and γ-cyclodextrin (γ-CD) were found to form inclusion complexes). Natamycin is the guest molecule in such inclusion complex in which the shape and size of the cup shape of part of the host molecule are critical to be able to form such complex. The concentration of the natamycin complexed with cyclodextrin in water is however still low, which limits the usability of this solution for various applications.

Thus, there is a need for pharmaceutical formulations having higher amounts of dissolved natamycin, without compromising the antifungal activity and/or without components that are undesired from a pharmaceutical point of view.

Further, when taken orally, little or no natamycin is absorbed from the gastrointestinal tract, making it inappropriate for treating systemic infections. Attempts to solubilize natamycin in vehicles that are safe for parenteral administration in humans have not yet been successful. Thus, there is also a need for effective natamycin formulations that are suitable for parenteral application.

The low solubility of natamycin also poses problems for its application as a food preservative. Although application of natamycin in crystalline form may in some cases be effective for that purpose, there is actually also a need for natamycin compositions comprising more finely divided forms of solid natamycin or natamycin that is completely dissolved. For example, the conventional application of natamycin as an aqueous suspension of crystals is undesired in view of the clogging of spray nozzles and the formation of a heterogeneous distribution when the suspension is applied on a surface (of e.g. cheese). Furthermore, more finely divided forms of natamycin or completely dissolved natamycin may allow the application of a lower dosage of natamycin for attaining the same antifungal effect.

A particular application of natamycin is the protection of agricultural products (in particular plant propagation material such as seed and flower bulbs) against fungi. The effectivity of natamycin however appears to be limited on such products, possibly because solid natamycin has limited access to fungi that reside in crevices or below the surface of the agricultural product. Natamycin that is either completely dissolved or that is present as smaller particles may therefore be more effective. On the other hand, existing fungicides such as thiram can be phytotoxic when applied in concentrations that are effective for combatting fungi. Also azole-fungicides generate resistance in targeted fungi, for example in *Aspergillus fumigatus* through 3 separate mutations since the early 90's. Natamycin is not prone to cause resistance development due to its mode of action directly on the ergosterol of the fungal cell membrane.

Thus, the low solubility of natamycin is an obstacle that needs to be overcome to attain a higher effectivity in several applications. Another advantage of a high concentration of dissolved natamycin is that natamycin stock solutions can be prepared.

SUMMARY OF THE INVENTION

It is therefore an objective of the present invention to provide natamycin that is in a form that is capable to effectively combat fungi. In particular, it is aimed to provide a composition of natamycin that has a higher concentration of natamycin than known compositions, and which composition is stable over a prolonged period of time.

The composition comprising natamycin at a high concentration can also be used as stock solutions to prepare compositions having lower concentration of natamycin, for example by diluting with water.

It is in particular an objective to provide an effective formulation of a bioactive molecule, in particular natamycin, that is suitable for medical application, for the preservation of foods and/or agricultural products against fungi.

DETAILED DESCRIPTION OF THE DRAWINGS

Figure 1:
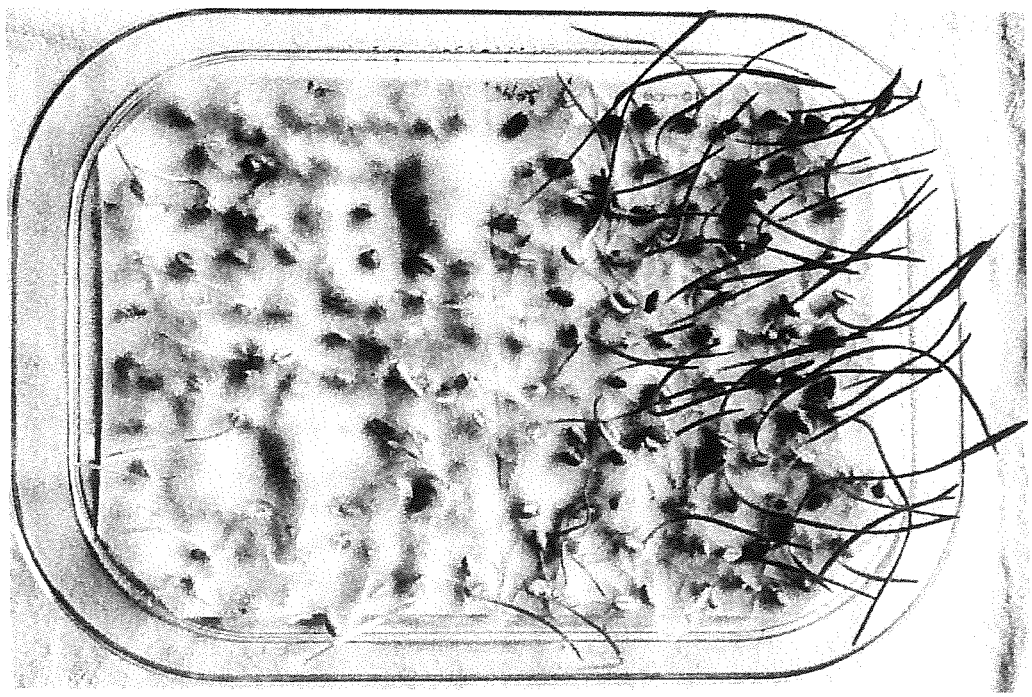
FIG. 1 is an image showing two test areas of Tartaros wheat seed naturally infected with fungus, wherein the left area contains untreated seed, while the right area contains the natamycin composition of entry 5.5 of Table 5, which is present in a concentration of 400 ppm on the seed.

It has now surprisingly been found that one or more of these objectives can be reached by a process for preparing a composition comprising a bioactive molecule comprising the steps of
  a. Dissolving a bioactive molecule having at least one acid group with a base at pH=>11 to obtain a solution A
  b. Neutralizing the solution A with an acid to obtain the composition comprising the bioactive molecule having a pH between 6 and 9, wherein PEG is added before the neutralizing step in case either the base and/or the acid is an inorganic compound.

The bioactive molecule can be present as the pure chemical component known from literature, or it can be present as an adduct with one of the components added to the process or formed during the process of preparing the composition according to the invention. In particular the bioactive molecule can be present as the reaction product of the pure component with the base (inorganic or organic base) which can give an ion pair having an increased solubility in an aqueous environment.

The term bioactive molecule here and hereinafter has to be understood to comprise both the pure bioactive molecule and any adduct which can be formed upon reaction with one of the components of the composition.

As an example natamycin may be present as the pure chemical molecule according to formula (I), or as an adduct with other components, like the base, acid and/or the optional PEG component.

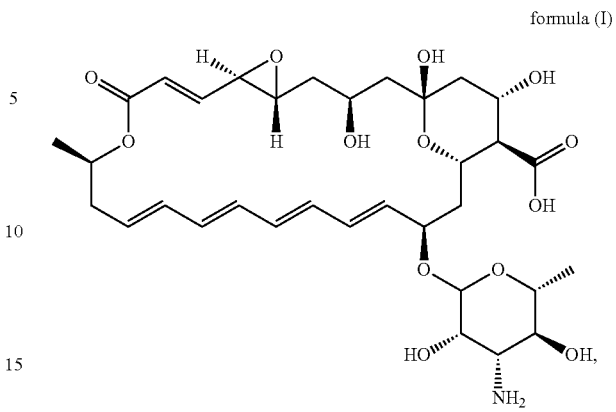

formula (I)

natamycin.

Without being wanted to be bound by any theory, it is believed that these adducts can be reversible and may have a higher solubility than the neutral natamycin and provide bioactive natamycin upon dilution or application to a biological system.

The term natamycin here and hereinafter has to be understood to comprise both the pure natamycin and any adduct which can be formed upon reaction with one of the components of the composition.

The bioactive molecule is preferably chosen from the group consisting of natamycin, amphotericin B, nystatin, filipin, giberrellic acid (GA3, GA4, GA7), auxin (indole-3-acetic acid), indole-3-butyric acid—abcissic acid (S-ABA) and betulinic acid. More preferably the bioactive molecule is chosen from natamycin and amphotericin B, most preferably bioactive molecule is natamycin.

In general, the amount of bioactive molecule ranges between 0.1-20 wt. %, relative to the total weight of the composition, more preferably between 1-18 wt. %, 3-12 or most preferably between 4 and 10 wt. %. Preferably the amount of water ranges between 5 and 45 wt. %, and/or the weight ratio between bioactive molecule and water is between 1:0.5 and 1:12. Preferably the composition contains PEG, preferably between 30 and 80 wt. % PEG having a number average molecular weight between 200 and 30000, or between 250 and 10000.

In case the bioactive molecule is natamycin, the ranges typically are between 0.1-20 wt. %, more preferably between 1-18 wt. %, 3-12 or most preferably between 4 and 10 wt. %, as described above. In case bioactive molecule is amphotericin-B, the max concentration may be lower. The typical concentration of amphotericin-B range between 0.1-10 wt. % or 0.2-5 wt. %.

All weight percentages are defined relative to the total of the composition, unless specified otherwise.

Water is present in the process according to the invention. The amount of water can vary within wide ranges. The amount of water may range between 5 and 80 wt. %, preferably between 5 and 45 wt. %. Preferably a composition is obtained having a high content of natamycin, and a limited amount of water. In a preferred embodiment, the weight ratio between natamycin and water is between 1:0.5 and 1:12, to ensure a composition having a high amount of natamycin. Preferably the weight ratio between natamycin and water is between 1:0.55 and 1:10, or between 1:0.6 and 1:9.

This composition is concentrated and can be diluted for further use.

In the first step of the process, deprotonation of the natamycin takes place by reaction of natamycin with a base. The base can be an inorganic base, like for example KOH or NaOH, an organic base, or mixtures thereof.

The pH of the resultant solution is above pH 11, preferably above pH 13.

Preferably an organic base is used to prepare an adduct of natamycin which is dissolved in water. Examples of organic bases are choline hydroxide, choline chloride, choline bitartrate, choline monohydrogen-tartrate, choline-dihydrogen-citrate, tetramethylammonium hydroxide, tetraethylammonium hydroxide, tetrabutylammonium hydroxide and bPEI (branched polyethyleneimine).

Preferably the organic base is choline hydroxide.

Choline hydroxide preferably is applied as a solution in water, for example as a mixture containing 45 wt. % choline hydroxide and 55 wt. % water, or for example as a mixture of 25 wt. % choline hydroxide in 75 wt. % water. This mixture can be used as a solvent mixture for the natamycin, such that the total composition comprises between 25 and 40 wt. % choline hydroxide.

The time needed to react natamycin with choline hydroxide should be sufficient for providing a clear solution A. The time typically ranges between 1 minute and 1 hour, or between 2 minutes and 30 minutes.

Choline hydroxide can also be added in more than 1 step, for example in 2 consecutive steps.

When an organic base is used, the base can be used to dissolve the natamycin, but the base can also act as a solvent for natamycin.

PEG can also be added as a cosolvent for natamycin after addition of base to the natamycin. In such cases the amount of choline hydroxide can range from 4-30 wt. %, for example between 10 and 25 wt. % relative to the total of the composition.

Preferably the PEG is a Poly Ethylene Glycol, which can have a number average molecular weight between 200 and 30000. In one embodiment PEG is applied having a lower molecular weight (for example between 200 and 1000, more preferably between 220 and 800 or between 250 and 600). In such cases PEG can be used as a liquid and compositions having excellent properties are obtained.

In another embodiment PEG having a molecular weight between 1000 and 10000 is applied. In such cases (especially at higher molecular weights, for example of at least from 5000, 6000 or 8000 to 10000) additional water may be needed to dissolve the high molecular weight PEG. The inventors found that in such cases natamycin may be present as dispersed crystals which can easily dissolve in the composition, rendering a composition having a quasi constant dissolved natamycin concentration: the composition contains dissolved natamycin and crystalline natamycin. When dissolved natamycin is taken from the composition, crystalline natamycin may be dissolved to generate the semi-constant natamycin concentration.

Compositions having lower molecular weight PEG (preferably between 200 and 1000) tend to be more stable compared to compositions having higher molecular weight PEG.

The weight ratio between natamycin and choline hydroxide may range between 1:0.4 and between 1:100, preferably between 1:0.45 and 1:20, or between 1:0.5 and 1:8. The lower ratios (for example 1:0.5-1:3) are preferably applied when also PEG is present as solvent, the higher ratios (for example 1:3-1:100) are applied in the absence of PEG or when a limited amount of PEG is present (for example between 0.1 and 15 wt. % PEG, relative to the total weight of the composition).

The weight ratio choline hydroxide and water needed to dissolve natamycin is at least 1.5, in order to have enough liquid to dissolve the natamycin. When the amount (weight) of water and choline hydroxide is less than 1.5 times the weight of natamycin, a paste or very high viscous substance is obtained which is less suitable for making the composition according to the invention.

In case the first step is carried out with an inorganic base (like for example KOH), than a PEG polymer should be added after formation of the ionic complex between natamycin and the inorganic base. The PEG assists in forming a stable complex, especially after step b of the process of the present invention.

If added, the amount of PEG may range between 0.5 and 90 wt. %, preferably between 20 and 87 wt. %, or between 30 and 80 wt. %.

Preferably the PEG is added at elevated temperature, preferably between 30 and 60° C. It is also possible to heat the PEG before addition of the mixture of natamycin and base component to a temperature between 40 and 85° C., to arrive at a solution A having a temperature between 30 and 60° C. A temperature of solution A below 30° C. may lead to a composition having an enhanced viscosity, or even a paste like consistency. A temperature above 80° C. may lead to excessive polymerization of PEG under the influence of KOH, which should preferably be avoided.

In the second step the reaction mixture is neutralized to a pH between 6 and 9 (preferably a pH between 7 and 8) by adding an acid component. The acid component can be an inorganic acid, like for example a solution of HCl, sulfuric acid and other strong acids, or the acid component can be an organic acid. Preferably the acid component used in step b is an organic acid.

Examples of organic acids are formic acid, acetic acid, propionic acid, sorbic acid, benzoic acid, lactic acid, malic acid, butanoic acid, hexanoic acid, hydroxybutanedioic acid, citric acid, fumaric acid, tartaric acid, ascorbic acid, octanoic acid and nicotinic acid. Preferably propionic acid is used for the neutralization of the solution A, when PEG is added to the composition.

In the absence of PEG, or when only low amounts (for example between 0.1 and 15 wt. %) of PEG are applied, preferably the organic acid is chosen from the group consisting of propionic acid, fumaric acid, malic acid, tartaric acid and lactic acid.

The amount of acid is determined by the amount of base added to the bioactive molecule, in order to arrive at a solution having a pH between 6 and 9, preferably between 6.5 and 8.5, most preferably between 7 and 8.

In case the acid is an inorganic acid, PEG should be added before the neutralisation step, as explained above. Neutralization step B preferably is performed within a time of 1-60 minutes after addition of PEG, more preferably between 2 and 30 minutes after the addition of PEG, or between 3 and 15 minutes after the addition of PEG.

The start of the neutralization of the reaction mixture should not be too late, in order to minimize possible side reactions between KOH and PEG, and/or side reactions between KOH and natamycin.

The amount of acid is determined by measuring the pH of the resulting composition comprising the bioactive molecule. In general the molar amount of the acid will be close to the molar amount of base.

In one embodiment, the invention relates to a process for preparing composition comprising natamycin comprising the steps of
a) Dissolving 0.1-20 wt. % of natamycin with an organic base dissolved in water at a pH of at least 13 to obtain a solution A,
b) Adding 30-90 wt. % polyethylene glycol having a molecular weight between 200 and 800 daltons, to obtain a solution A',
c) Neutralizing the solution A' with an aqueous solution of an inorganic acid to obtain the composition comprising natamycin having a pH ranging from 6 to 9, preferably between 7 and 8,
wherein the organic base is chosen from the group consisting of choline hydroxide, tetramethyl ammonium hydroxide, tetra ethyl ammonium hydroxide.

In a preferred embodiment, the invention relates to a process for preparing a composition comprising natamycin comprising the steps of
a) Dissolving 0.1-20 wt. % of natamycin with an 5-35 wt. % of an organic base dissolved in water at a pH of at least 13 to obtain a solution A,
b) Neutralizing the solution A with an organic acid to obtain the composition comprising natamycin having a pH ranging from 6 to 9, preferably between 6.5 and 8.5 or between 7 and 8,
wherein the organic base is chosen from the group consisting of choline hydroxide, tetramethyl ammonium hydroxide, tetra ethyl ammonium hydroxide and wherein the organic acid is chosen from propionic acid, citric acid, fumaric acid, malic acid, lactic acid, hexanoic acid or tartaric acid.

Preferably the organic base is choline hydroxide. Preferably the organic acid is propionic acid. Optionally 0.5-90 wt. % of PEG may be added to solution A or A' or after the neutralization step. Preferably the PEG has a molecular weight between 200 and 800. The composition preferably contains between 5 and 45 wt. % of water.

During step a) of the process according to the invention, generally an orange/brown colored solution is obtained. During the neutralization step the color becomes lighter when the pH drops. The color change is an indication for achieving a composition having a pH close to neutral. The actual pH value of the aqueous composition can be determined with known means, like for example pH indicator paper.

In a preferred embodiment, the invention relates to a process for preparing a composition comprising natamycin comprising the steps of
a) Dissolving 0.1-20 wt. % of natamycin with 5-35 wt. % of choline hydroxide dissolved in water at a pH of at least 13 to obtain a solution A,
b) Neutralizing the solution A with propionic acid to obtain the composition comprising natamycin having a pH ranging from 6 to 9, preferably between 7 and 8.

Optionally 0.5-90 wt. % of PEG may be added to solution A or after the neutralizing step. Preferably the PEG has a molecular weight between 200 and 800. The composition preferably contains between 5 and 45 wt. % of water.

In a preferred embodiment the invention relates to a process for preparing a composition comprising natamycin comprising the steps of
a) Dissolving 4-10 wt. % of natamycin with 5-30 wt. % of choline hydroxide dissolved in water at a pH of at least 13 to obtain a solution A,
b) Adding an aqueous choline hydroxide solution which is neutralized with propionic acid to obtain solution A',
c) Neutralizing the solution A' with propionic acid to obtain composition comprising natamycin having a pH ranging from 6 to 9, preferably between 7 and 8,
wherein the neutralized choline hydroxide solution is prepared from a choline hydroxide solution having between 15 and 50 wt. % choline hydroxide in water, preferably from 25-45 wt. % choline hydroxide in water.

In a preferred embodiment, the invention relates to a process for preparing a composition comprising natamycin comprising the steps of
a) Dissolving 4-10 wt. % of natamycin with 5-35 wt. % of choline hydroxide dissolved in water at a pH of at least 13 to obtain a solution A,
b) Neutralizing the solution A with propionic acid to obtain composition comprising natamycin having a pH ranging from 6 to 9, preferably between 7 and 8.

Optionally 0.5-30 wt. % of PEG may be added to solution A or after the neutralizing step. Preferably the PEG has a molecular weight between 1000 and 10000 and is dissolved in an equal amount of water before adding to the process. The composition preferably contains between 5 and 45 wt. % of water.

In an embodiment, the invention relates to a process for preparing a composition comprising natamycin comprising the steps of
a) Dissolving 0.1-20 wt. % of natamycin with 0.5-2.5 wt. % of potassium hydroxide dissolved in water at a pH of at least 13 to obtain a solution A,
b) Adding 30-80 wt. % polyethylene glycol having a molecular weight between 200 and 800 daltons, to obtain a solution B,
c) Neutralizing the solution B with propionic acid to obtain the composition comprising natamycin having a pH ranging from 6 to 9, preferably between 7 and 8.

The composition preferably contains between 5 and 45 wt. % of water.

When an inorganic base is used to dissolve natamycin, it is possible to add less strong organic bases to make a stable composition. An example of such bases are amines and imines, like for example bPEI, which is a branched polyethyleneimine.

The invention also relates to a composition comprising the reaction product of 0.1-20 wt. % of natamycin, 5-30 wt. % of choline hydroxide and an organic acid, wherein the organic acid is selected from propionic acid, fumaric acid, malic acid, tartaric acid and lactic acid. The composition may further contain 5-90 wt. % water, between 0-85 wt. % PEG and additives. Preferably the composition comprises the reaction product between 4-10 wt. % natamycin, between 5 and 10 wt. % choline hydroxide, 50-85 wt. % PEG having a molecular weight between 200 and 800 daltons, and the organic acid, wherein the composition comprises between 5-45 wt. % water, preferably 5-20 wt. % water.

The composition preferably comprises 1-18 wt. % natamycin, or 3-12 wt. % or 4-10 wt. %, relative to the total composition.

The weight ratio between natamycin and water is preferably between 1:0.5 and 1:12.

The weight ratio between natamycin and choline hydroxide is preferably between 1:0.4 and 1:100. Preferably the composition comprises between 5 and 45 wt. % water.

The composition of the invention may contain additives, in particular additives for improving the look and feel of the product once it contains the composition. In the case of seed, for example, it may comprise anti-sticking agents, agents that improve the flowability of the seed and/or agents that improve the optical appearance of the seed such as pigments and shining agents.

Accordingly, the invention further relates to a method for treating an agricultural product or a food product, comprising applying a composition of the invention on an agricultural product or a food product, respectively.

The invention further relates to an agricultural product or food product obtainable by such method.

The invention further relates to an agricultural product or food product comprising a composition of the invention.

A composition of the invention may also find application in the medical field. Therefore, the invention further relates to a composition of the invention for medical use. The invention in particular relates to a corn position of the invention for the treatment of a fungal infection. The composition may for example be used as a cream or potage to treat topical infections, for example of the skin or mucus, such as in the genital area. The action of the composition may also be enteral or parenteral. Preferably, the auxiliary compound in the composition comprises a pharmaceutically acceptable polymer, e.g. PEG.

Materials and Methods

Use is Made of the Following Experimental Procedures

1) Preparing the Natamycin Compositions

The compositions comprising natamycin were prepared as 100 g formulations. Exemplary is the preparation of a formulation comprising 5 wt % of natamycin (50,000 ppm). The natamycin is supplied by Shandong Freda Biotechnology Co., Ltd. The natamycin used is of >90% purity, therefore 5.5 grams of this natamycin is used for the preparation of 100 g formulations. All other materials, except thiram, are supplied by Acros Organics. Water used is tap water.

During the preparation, natamycin is dissolved at pH 13-14 by adding an alkaline solution of an anorganic base such as KOH (7 wt. %-25 wt. %) of or an organic base such as choline hydroxide (25 wt. %-45 wt. %). Heated PEG-200, supplied by Acros Organics or an additional amount of organic base can be added. Thereafter neutralization to pH 6.5-8 or other pH is performed with an organic acid such as propionic acid. Organic acids are liquid (e.g. propionic acid 98% and lactic acid aqueous solution 85%) or in powder/crystalline form (fumaric acid, malic acid, tartaric acid). Solid organic acids require a longer mixing and neutralization time than liquid organic acids.

A 150 mL glass vessel is used for the preparation steps. A magnetic stirrer is used for mixing materials whenever the viscosity is low enough. A spoon is used for mixing higher viscosity mixtures, especially when mixing natamycin powder with the first amount of alkaline solution. Adding too much alkaline solution in 1 step can create lumps of natamycin, which are difficult to dissolve. A glass vessel is used for heating PEG-200 in a magnetron upon which the temperature is measured with an infra-red thermometer. The pH is measured using pH indicator paper. Before neutralization the pH is often found to be above pH 13. During neutralization the color of the mixture is becoming lighter below pH 10, the color is especially lighter in the target pH range. Also the viscosity of the mixture is reducing at the same time the color is lightening. The final solution is mostly clear and off red-brown in color.

Upon 12× dilution with 11 parts of water mixed with 1 part of natamycin solution the dilution can show crystallization after a period of several hours to 24 hours. The dilution ratio of 12× is chosen as this dilution rate appears to show relatively more crystallization than other dilution ratio's. It is also a ratio that maybe used to produce solutions from stock solutions under practical conditions.

EXAMPLE 1

Different compositions according to the present invention have been prepared with PEG 200 and PEG 6000 as polymers, choline hydroxide as base and propionic acid as neutralizing compound. Composition shave been prepared with 5 to 20 wt. % natamycin, which all show to be stable.

The results are shown in table 1.

In each experiment a correction has been made for the purity of natamycin. For example if a composition is prepared having 5 wt. % natamycin, and the purity of natamycin is 90%, the amount of natamycin (90%) is 5/0.9=5.55 g/100 g of composition. In this example >90% purity natamycin, supplied by Shandong Freda Biotechnology Co., Ltd., is used. The amount of natamycin is weighed in a glass vessel of 150 ml. The suitable amount of choline hydroxide 45 wt. % aqueous solution, supplied by Acros Organics, is added in 1 or 2 steps to the natamycin. In the first step not more than 1.5× the amount of natamycin is added to make a smooth mixture. If water is used this is added after the amount of choline hydroxide has been mixed with the natamycin. The water facilitates obtaining a light brown solution. When no water is used the result of the dissolving step maybe a mixture with a paste constitution. PEG-200 is heated in a glass vessel in a magnetron to the described first temperature. The temperature is measured after mixing by an infra-red thermometer. The heated PEG-200 is added to the mixture of natamycin, choline hydroxide solution and optionally water. A spoon and then magnetic stirrer is used to process this mixture into a uniform solution. The temperature is measure again and indicated as the second temperature value. The color of the solution is dark reddish brown with a pH higher than 13. The warm mixture is then neutralized to pH 6.5-8 by adding with a syringe the indicated amount of liquid propionic acid of 98% purity. During the neutralization the color of the solution is becoming lighter below pH 10. The pH is measured again using pH indicator paper. The propionic acid neutralizing agent is added after the addition of PEG At higher concentrations of natamycin the PEG needs to be of higher temperature for sufficient temperature increase of the mixture to obtain clear solutions including PEG.

Higher molecular weight PEG's such as PEG-6000 or PEG-1500 can be used after dissolving in approximately equal amount of water and heating. The viscosity of the final solution after storage during several days using higher molecular weight PEG will be relatively higher.

The final solution is reddish-brown in color, from low viscosity to higher viscosity depending on the concentration of natamycin and forming stable solutions.

Upon 12× dilution with 11 parts of water mixed with 1 part of natamycin solution the dilution can show crystallization after a period of several hours to 24 hours.

TABLE 1 examples according to the invention.

| | 1.1 | 1.2 | 1.3 | 1.4 | 1.5 | 1.6 | 1.7 | 1.8 | 1.9 |
|---|---|---|---|---|---|---|---|---|---|
| Natamycine 90% purity (Wt %) | 5.6 | 7.4 | 8.3 | 5.6 | 8.3 | 11.1 | 16.7 | 22.2 | 5.6 |
| Polymer | PEG200 | PEG200 | PEG200 | PEG200 | PEG200 | PEG200 | PEG200 | PEG200 | PEG6000 |
| Final conc. Polymer (Wt %) | 78.0 | 78.4 | 78.0 | 30.0 | 75.7 | 72.1 | 63.8 | 48.6 | 20.0 |
| Temperature before mixing | 57' C. → 44' C. | 63' C. → 37' C. | 83' C. → 47' C. | 20' C. → 39' C. | 63' C. → 42' C. | 83' C. → 45' C. | 83' C. → 45' C. | 83' C. → 42' C. | 67' C. → 40' C. |
| base | choline OH | choline OH | choline OH | choline OH | choline OH | choline OH | choline OH | choline OH | choline OH |
| amount base (Wt %) | 3.35 | 4.3 | 4.95 | 22.5 | 4.9 | 6.3 | 7.4 | 10.8 | 19.2 |
| water (Wt %) | 11.6 | 7.7 | 6.05 | 27.5 | 9 | 7.7 | 9.1 | 13.2 | 43.4 |
| Neutralizing agent | propionic acid | propionic acid | propionic acid | propionic acid | propionic acid | propionic acid | propionic acid | propionic acid | propionic acid |
| Amount neutralizing agent (Wt %) | 1.4 | 2.2 | 2.65 | 14.4 | 2.1 | 2.8 | 3 | 5.2 | 11.8 |
| ratio (w/w) Natam/polymer | 1/15.6 | 1/15.8 | 1/15.6 | 1/6 | 1/10.1 | 1/7.2 | 1/4.2 | 1/2.45 | 1/4 |
| clear or turbid | clear | slightly milky | slightly milky | clear | clear | clear | clear | turbid | clear |
| Color | reddish brown | reddish brown | reddish brown | dark reddish brown | dark reddish brown | dark reddish brown | dark reddish brown | dark reddish brown | light brown |
| Viscosity (indication) | low | low | low | low | medium | medium | high | very high | low |
| Stability (visual) | ●●●●● | ●●●● | ●●●● | ●●●●● | ●●● | ●●●●● | ●●●●● | ●●●● | ●●●●● |
| Crystals or other structures in 12x dilution with water after 24 hours (visual) | ●●●●● | | | ●●●●● | | | | | ●●●●● |

| Stability (visual) | | Crystals or other structures in 12x dilution with water after 24 hours (visual) | |
|---|---|---|---|
| ●●●●● | Clear | ●●●●● | Clear |
| ●●●● | Slightly milky | ●●●● | Slight cloud of crystals |
| ●●● | Milky, later some sediment | ●●● | Cloud of crystals |
| ●● | Sediment | ●● | Layer of crystals |
| ● | Large amount of sediment | ● | Thick layer of crystals |

All compositions have a high amount of natamycin, are stable and do not crystallize.

EXAMPLE 2

Example 2 shows compositions comparable to the compositions in example 1, but prepared in a different order: neutralization with propionic acid is performed before the addition of PEG.

The results are summarized in table 2.

TABLE 2

| | 2.1 | 2.2 | 2.3 | 2.4 | 2.5 | 2.6 |
|---|---|---|---|---|---|---|
| Natamycine 90% purity (Wt %) | 5.60 | 5.60 | 5.60 | 5.60 | 11.10 | 5.60 |
| Polymer | PEG200 | PEG200 | PEG200 | PEG200 | PEG200 | PEG300 |
| Final conc. Polymer (Wt %) | 48.7 | 48.7 | 69.4 | 29.4 | 44.2 | 47.9 |
| Temperature before mixing | 87' C. -> 48' C. | 20' C. -> 32' C. | 57' C. -> 47' C. | 60' C. -> 40' C. | 97' C. -> 52' C. | 60' C. -> 42' C. |
| base | choline OH | choline OH | choline OH | choline OH | choline OH | choline OH |
| amount base (Wt %) | 16.2 | 16.2 | 9 | 22.5 | 16.2 | 16.3 |
| water (Wt %) | 20 | 20 | 11 | 27.5 | 20 | 20.1 |
| Neutralizing agent | propionic acid | propionic acid | propionic acid | propionic acid | propionic acid | propionic acid |
| Amount neutralizing agent (Wt %) | 9.5 | 9.5 | 5 | 15 | 8.5 | 10.1 |
| ratio (w/w) Natam/polymer | 1/9.8 | 1/9.8 | 1/13.8 | 1/6 | 1/9 | 1/9.6 |
| clear or turbid | clear | clear | clear | clear | clear | clear |
| Color | dark reddish brown | dark reddish brown | dark reddish brown | dark reddish brown | dark reddish brown | dark reddish brown |
| Viscosity (indication) | low | low | low | low | low | low |
| Stability (visual) | ●●●●● | ●●●●● | ●●● | ●●●●● | ●●●●● | ●●●●● |

TABLE 2-continued

|  | 2.1 | 2.2 | 2.3 | 2.4 | 2.5 | 2.6 |
|---|---|---|---|---|---|---|
| Crystals or other structures in 12x dilution with water after 24 hours (visual) |  |  | •• | ••••• |  |  |

EXAMPLE 3

Experiments are performed with different organic acids, for neutralizing the natamycin solutions.

Results are shown in table 3.

The natamycin amount used is calculated from its purity. In this example >90% purity natamycin, supplied by Shandong Freda Biotechnology Co., Ltd., is used. The amount of natamycin for most objects is 5.5 grams, weighed in a glass vessel of 150 ml. The suitable amount of choline hydroxide 45% aqueous solution is added in 1 or 2 steps to the natamycin.

In the first step not more than 1.5x the amount of natamycin is added to make a smooth mixture. After this addition, the natamycin—choline hydroxide mixtures are further diluted with additional choline hydroxide (45 wt. % in water).

In a final step, all compositions are neutralized with organic acids under stirring with a magnetic stirrer. The final pH is confirmed using a pH indicator paper. The reaction temperature during neutralization ranged between 35'C.-47'C.

The solutions are visually observed for color, clarity/turbidity and viscosity. Solutions are diluted 12x with water by mixing 11 parts of water with 1 part of solution. Crystal formation in this dilution is visually checked after 6 hours and 24 hours.

| Bio-activity Antifungal |  | Plant growth |  |
|---|---|---|---|
| ••••• | No fungi growth | ••••• | Healthy growth |
| •••• | Little, slow fungi growth | •••• | Some abnormal growth |
| ••• | Fungi growth | ••• | Abnormal growth |
| •• | Fungi growth covering some seeds | •• | Many abnormal growth |
| • | Heavy fungi growth covering all seeds | • | Almost no growth |

The compositions of example 3 have been tested as dilutions for its bioactivity (antifungal) and support of plant growth.

The bio-activity of compositions on fungi is determined at various dilutions on the growth and survival of *Aspergillus niger* spores. The growth of the *Aspergilus niger* culture is measured by OD (optical density) by OD600.

Method

*Aspergillus niger* spores and the medium are added to a 96-wells plate and incubated to germinate the spores. After germination of spores the formulation is added in triplo in various dilutions together with additional medium and an amount of luciferine. The well plate is incubated in a plate-reader that measures every 5 minutes both the OD as well as the emitted luminescence.

TABLE 3

|  | 3.1 | 3.2 | 3.3 | 3.4 | 3.5 | 3.6 | 3.7 |
|---|---|---|---|---|---|---|---|
| Natamycine 90% purity (Wt %) | 5.6 | 5.6 | 5.6 | 5.6 | 5.6 | 5.6 | 5.6 |
| Polymer | none | none | none | none | none | none | none |
| Final conc. Polymer (Wt %) | 0 | 0 | 0 | 0 | 0 | 0 | 0 |
| Temperature before mixing | 20' C. → 42' C. | 20' C. → 39' C. | 20' C. → 39' C. | 20' C. → 45' C. | 20' C. → 39' C. | 20' C. → 39' C. | 20' C. → 37' C. |
| base | choline OH | choline OH | choline OH | choline OH | choline OH | choline OH | choline OH |
| amount base (Wt %) | 33.5 | 32.4 | 34.5 | 33.6 | 30.6 | 29.1 | 33.3 |
| Water (Wt %) | 40.7 | 39.5 | 41.9 | 40.8 | 37 | 35.3 | 40.1 |
| Neutralizing agent | propionic acid | citric acid | fumaric acid | malic acid | lactic acid 85% | hexanoic acid | tartaric acid |
| Amount neutralizing agent (Wt %) | 20.2 | 22.5 | 18 | 20 | 26.8 | 30 | 21 |
| ratio (w/w) Natam/polymer | 1/0 | 1/0 | 1/0 | 1/0 | 1/0 | 1/0 | 1/0 |
| clear or turbid | clear | clear | clear | clear | clear | clear | clear |
| Color | light brown color | light brown color | light brown color | light brown color | light brown color | light brown color | light brown color |
| Viscosity | low | low | low | low | low | low | low |
| Stability | stable | stable; pH 6.4; dark brown after storage | stable | stable | stable | stable | stable; after 10 days still not very dark |
| Crystal or other structures formation in 12x dilution with water | after 24 hours: ••••• | after 6 hours: •• | after 24 hours: •••• | after 6 hours: •••• | after 24 hours: •••• | after 2 hours: • | after 24 hours: ••••• |
| Bio-activity Antifungal | ••••• | •••• | ••••• | •••• | ••••• | ••••• | ••••• |
| Plant growth | ••••• | •••• | ••••• | •••• | •••• | • | ••••• |

The antifungal activity and plant growth results of the different examples have been visually inspected. High antifungal activity is rated as 5 dots, while poor antifungal activity is indicated with a single dot.

Excellent plant growth stimulation is indicated with 5 dots, while poor plant growth is indicated with a single dot.

EXAMPLE 4

Compositions have been prepared with different organic bases. Results are shown in table 4.

The natamycin amount used is calculated from its purity. In this example >90% purity natamycin, supplied by Shandong Freda Biotechnology Co., Ltd., is used. For most objects the amount of 5.5 grams natamycin of 90% purity is weighed in a glass vessel of 150 ml. The suitable amounts of choline hydroxide 45% aqueous solution is added in 1 or 2 steps to the natamycin.

In the first step not more than 1.5× the amount of natamycin is added to make a smooth mixture.

25 wt. % aqueous solutions of tetra ethyl ammonium hydroxide and tetra methyl ammonium hydroxide were supplied by Acros Organics. These is added in 2-3 steps to the natamycin and mixed in with a spoon.

PEG-200 is heated in a glass vessel in a magnetron to the described first temperature. The temperature is measured after mixing by an infra-red thermometer. The heated PEG-200 is added to the mixture of natamycin, tetra ethyl ammonium hydroxide solution. A spoon and then magnetic stirrer is used to process this mixture into a uniform solution.

All objects are finally neutralized with organic acids under stirring with a magnetic stirrer. The final pH is confirmed using a pH indicator paper. The final temperature of all objects is in a range of 30'C-50'C.

The solutions are visually observed for color, clarity and viscosity. Solutions are diluted 12× with water by mixing 11 parts of water with 1 part of solution. Crystal formation in this dilution is visually checked after 24 hours.

Comparative experiment B shows the effect of dissolving natamycin with KOH, and subsequently neutralizing with HCl, but in the absence of PEG. No suitable composition could be obtained having a high dissolved natamycin concentration.

The natamycin amount used is calculated from its purity. In this example >90% purity natamycin, supplied by Shandong Freda Biotechnology Co., Ltd., is used. For these experiments the amount of 5.5 grams natamycin of 90% purity is weighed in a glass vessel of 150 ml. The suitable amounts of water or potassium hydroxide aqueous solution is added in 1 or 2 steps to the natamycin. In the first step not more than 1.5× the amount of natamycin is added to make a smooth mixture.

PEG-200 is heated in a glass vessel in a magnetron to the described first temperature. The temperature is measured after mixing by an infra-red thermometer. The heated PEG-200 is added to the mixture of natamycin, potassium hydroxide solution or water. A spoon and then magnetic stirrer is used to process this mixture into a uniform solution or suspension in case of comparative experiment A.

All experiments with alkaline solution are finally neutralized with HCL 10% solution or propionic acid to pH 6.5-8 under stirring with a magnetic stirrer. The final pH is confirmed using a pH indicator paper. The final temperature of all experiments can be high when putting for a second time in the magnetron.

The bio-activity of compositions on fungi is determined at various dilutions on the growth and survival of *Aspergillus niger* spores. The growth of the *Aspergilus niger* culture is measured by OD (optical density) by OD600.

The bioactivity of compositions on oomycetes is determined at 10× dilution ratio's used with a culture of *Phytophtora infestans* on plates by judging the growth and survival of the *P. infestans* by visual inspection by a skilled microbiologist.

TABLE 4 examples with different organic bases including tetraethylammoniumhydroxide and tetramethylammoniumhydroxide.

|  | 1.1 | 1.2 | 4.1 | 4.2 | 4.3 | 5.0 |
| --- | --- | --- | --- | --- | --- | --- |
| Natamycine 90% purity (Wt %) | 5.60 | 7.40 | 5.60 | 7.40 | 7.40 | 5.60 |
| Polymer | PEG200 | PEG200 | PEG200 | PEG200 | PEG200 | PEG200 |
| Final conc. Polymer (Wt %) | 78 | 78 | 78 | 65 | 65 | 61 |
| Temperature before mixing | 57' C. → 44' C. | 63' C. → 37' C. | 57' C. | 57' C. | 57' C. | 70' C. → 50' C. |
| base | choline OH | choline OH | TEAOH | TEAOH | TMAOH | KOH + bPEI |
| amount base (Wt %) | 3.4 | 4.3 | 3.8 | 6.3 | 6.3 | 1.6 + 8 |
| water (Wt %) | 11.6 | 8.1 | 11.3 | 18.6 | 18.8 | 14.8 |
| Neutralizing agent | propionic | propionic | propionic | lactic 85% | propionic | propionic |
| Amount neutralizing agent (Wt %) | 1.4 | 2.2 | 1.25 | 2.75 | 2.0 | 9.0 |
| ratio (w/w) Natam/polymer | 1/15.6 | 1/15.6 | 1/15.6 | 1/13 | 1/13 | 1/12.2 |
| clear or turbid | clear | slightly milky | clear | clear | clear | clear |
| Color | reddish brown | reddish brown | light brown color | dark red-brown color | dark red-brown color | dark red-brown color |
| Viscosity (visual) | low | low | low | low | low | low |
| Stability (visual) | ••••• | ••••• | ••••• | ••••• | ••••• | ••••• |
| Crystal formation in 12x dilution with water after 24 hours (visual) | ••••• |  | •• |  | ••••• | ••••• |

EXAMPLE 5

Table 5.1 shows examples of compositions prepared with an inorganic base (KOH) instead of the preferred organic base. Also two comparative exaperiments have been added: comparative experiment A describes an experiment, where no base is added, but only PEG was added to the natamycin: no soluble composition could be obtained.

In the absence of use of an alkali solution the composition is a suspension which is unstable and forms a deposit of crystals at the bottom. The bio-activity against fungi is average and the bioactivity against oomycetes is low. Example 5.3 shows good bio-activity against fungi and a fairly good bioactivity against oomycetes. A high temperature combined with a high concentration of alkali solution for example 5.3 and 5.4 reduces the bioactivity against fungi to a very low level.

Table 5.2 shows examples of compositions prepared with KOH and in addition bPEI (branched polyethylene-imine) molecular weight 600 supplied by Polysciences Europe GmbH.

The bPEI is introduced in the process after dissolving natamycin with KOH solution. A 50% bPEI aqueous solution is mixed with the KOH-natamycin mixture. Thereupon the process is continued by adding heated PEG and finally the neutralization step.

TABLE 5.1

Use of KOH as base.

|  | A | B | 5.1 | 5.2 | 5.3 | 5.4 | 5.5 |
|---|---|---|---|---|---|---|---|
| Natamycine 90% purity | 5.6 | 5.6 | 5.6 | 5.6 | 5.6 | 5.6 | 5.6 |
| Polymer | PEG200 | None | PEG6000 | PEG200 | PEG200 | PEG200 | PEG6000 |
| Final conc. Polymer (Wt %) | 80 | 0 | 35 | 81 | 79 | 89 | 34 |
| Temperature before mixing | 84' C. → 55' C. |  | 86' C. → 48' C. | 80' C. → 51' C. | 79' C. → 53' C. | 110' C. → 100' C. | 50' C. → 35' C. |
| type of base | none | KOH | KOH | KOH | KOH | KOH | KOH |
| base (Wt %) | 0 | 1.05 | 1.05 | 1.25 | 3.1 | 1.3 | 1.05 |
| Water (Wt %) | 14.4 | 88.4 | 53 | 11.2 | 9.4 | 3.7 | 54 |
| Neutralizing agent | none | HCL 10% sol. | HCL 10% sol. | propionic acid | propionic acid | propionic acid | HCl 10% sol |
| Amount neutralizing agent (Wt %) | 0 | 5 | 5 | 1 | 2.5 | 1 | 5 |
| ratio (w/w) Natam/polymer | 1/16 | 1/0 | 1/7 | 1/16.2 | 1/16 | 1/17.8 | 1/7 |
| clear or turbid | turbid | turbid | turbid | dark | black | black | turbid |
| Color | white | white | brown-yellow | dark red brown | very dark reddish brown | very dark reddish brown | brown yellow |
| Viscosity | Low viscocity | Very high viscosity | Medium viscosity | Low viscosity | Medium viscosity | Medium viscosity | high |
| Stability | Not stable. Settling in layer of crystals. | Paste. | Not stable. Sediment and higher viscosity. | A little sediment after storage | Becoming more viscous. Stable. | Stable |  |
| Bioactivity on fungi | ••• |  | ••••• | ••••• | •• | •• | •• |
| Bioactivity on oomycetes | • |  | • | •••• | ••••• | •••• |  |

TABLE 5.2

Use of KOH and bPEI as bases.

|  | 5.6 | 5.7 | 5.8 | 5.9 | 5.10 |
|---|---|---|---|---|---|
| Natamycine 90% purity (Wt %) | 5.60 | 5.60 | 5.60 | 5.60 | 5.60 |
| Polymer | PEG200 | PEG200 | PEG200 | PEG200 | PEG200 |
| Final conc, Polymer (Wt %) | 61 | 67 | 70 | 74 | 75 |
| Temperature before mixing | 70' C. → 50' C. | 72' C. → 50' C. | 72' C. → 50' C. | 72' C. → 50' C. | 75' C. → 55' C. |
| base | KOH + bPEI | KOH + bPEI | KOH + bPEI | KOH + bPEI | KOH + bPEI |
| amount base (Wt %) | 1.6 + 8 | 1.6 + 6 | 1.6 + 4 | 1.6 + 2 | 1.6 + 1 |
| water (Wt %) | 15 | 15 | 15 | 15 | 15 |
| Neutralizing agent | propionic | propionic | propionic | propionic | propionic |
| Amount neutralizing agent (Wt %) | 9.0 | 5.0 | 3.5 | 2.5 | 2.1 |
| ratio (w/w) Natam/polymer | 1/12.2 | 1/13.4 | 1/14 | 1/14.8 | 1/15 |
| clear or turbid | clear | clear | clear | clear | clear |
| Color | dark red-brown color | dark red-brown color | dark red-brown color | dark red-brown color | dark red-brown color |
| Viscosity (visual) | low | low | low | low | low |
| Stability (visual) | ••••• | ••••• | ••••• | ••••• | ••••• |
| Crystal formation in 12x dilution with water after 24 hours (visual) | ••••• | ••••• | ••••• | ••••• | ••••• |

| Bioactivity on fungi spores | | Bioactivity on oomycetes spores | |
| --- | --- | --- | --- |
| ●●●●● | Complete control at >1500x dilution | ●●●●● | Complete control at 150x dilution |
| ●●●● | Complete control at 1500x dilution | ●●●● | Complete control at 150x dilution for limited |
| ●●● | Complete control at <1500x dilution | ●●● | Reduction of oomycetes growth |
| ●● | Reduction of fungi growth | ●● | Limited reduction of oomycetes growth |
| ● | No reduction of growth | ● | No reduction of growth |

EXAMPLE 6

In example 6 three different bioactive molecule have been dissolved with the method according to the present invention.

Betulinic acid—98% is supplied by Xi'an Lyphar Biotech Co., LTD;

Amphotericin-B—86% is supplied by XI'AN HEALTH BIOCHEMICAL TECHNOLOGY CO., LTD;

Gibberellic acid GA3—90% is supplied by BIOSYNTH AG.

Compositions have been prepared by taking the bioactive component, adding the base with water to dissolve the bioactive compound, followed by adding warm PEG. After stirring to make a clear solution, the neutralizing agent has been added to prepare the solution of the bioactive.

Results are summarized in table 6.

TABLE 6

| | 6.1 | 6.2 | 6.3 |
| --- | --- | --- | --- |
| Bioactive | Betulinic acid | Amphotericin-B | Gibberellic acid GA3 |
| Final conc bioactive (Wt %) | 2.0 | 2.5 | 10.0 |
| Polymer | PEG200 | PEG200 | PEG200 |
| Final conc. Polymer (Wt %) | 92 | 84 | 56 |
| Temperature before mixing | 100' C. → 75' C. | 100' C. → 75' C. | 60' C. → 40' C. |
| base | choline OH | KOH | KOH |
| amount base (Wt %) | 1.1 | 0.7 | 2 |
| Water (Wt %) | 4.1 | 9.8 | 23 |
| Neutralizing agent | propionic acid | sulphuric acid 10% sol. | HCl 10% sol. |
| Amount neutralizing agent (Wt %) | 0.5 | 3.5 | 9 |
| ratio (w/w) Bioactive/polymer | 1/46 | 1/33.4 | 1/5.6 |
| clear or turbid | clear | clear | clear |
| Color | yellowish | very dark, reddish | very slight yellow |
| Viscosity | Low viscocity | Low viscosity | Low viscosity |
| Stability | Stable. | Stable | Stable |

EXAMPLE 7

Treating Seed with a Natamycin Composition

The seeds were treated with the natamycin composition were typically prepared as a 400 ppm mixture, i.e. a mixture comprising 0.4 g of natamycin per kg of seed. For example, when a composition comprising 5 wt. % of natamycin was used (50,000 ppm), 0.16 g of the composition was first diluted to a weight of 2.0 g (4,000 ppm). Then, this diluted mixture was applied to 20 g of seed. The water evaporated during 8 hours in the air at room temperature, yielding a portion of seeds comprising 400 ppm of natamycin.

Comparative experiments were carried out with thiram, using a 42-S formulation obtained from Bayer Cropscience in the USA containing 42% thiram. This solution was diluted by adding water to 0.16 g of the thiram solution until it reached the weight of 2 g. Then, this diluted mixture was applied to 20 g of seed. A coating around the seeds was obtained by allowing the solvent to evaporate during 8 hours in the air at room temperature, yielding a portion of seeds comprising 3.36 g of thiram per kg of seed (3360 ppm). A second formulation on seed was prepared comprising 0.840 g of thiram per kg of seed (840 ppm).

The seeds were then placed on germination paper (paper obtained from Allpaper BV, type T10 D 140*200, 550 g/m-2) and the growth of fungus was monitored as the seeds germinated, typically during 7-30 days at room temperature. In comparative experiments, untreated infected seeds or thiram-treated infected seeds were used. The results of this essay are as effectivities of the growth inhibition of fungus compositions, represented on a scale of 1-5 (1=no effect; 2=small effect; 3=standard effect; 4=good effect; 5=excellent effect). The effect of the composition on the growth of the plant is represented on a scale of 1-5 (1=strong negative effect; 2=fairly strong negative effect; 3=small negative effect; 4=no effect; 5=positive effect).

Figure 2:
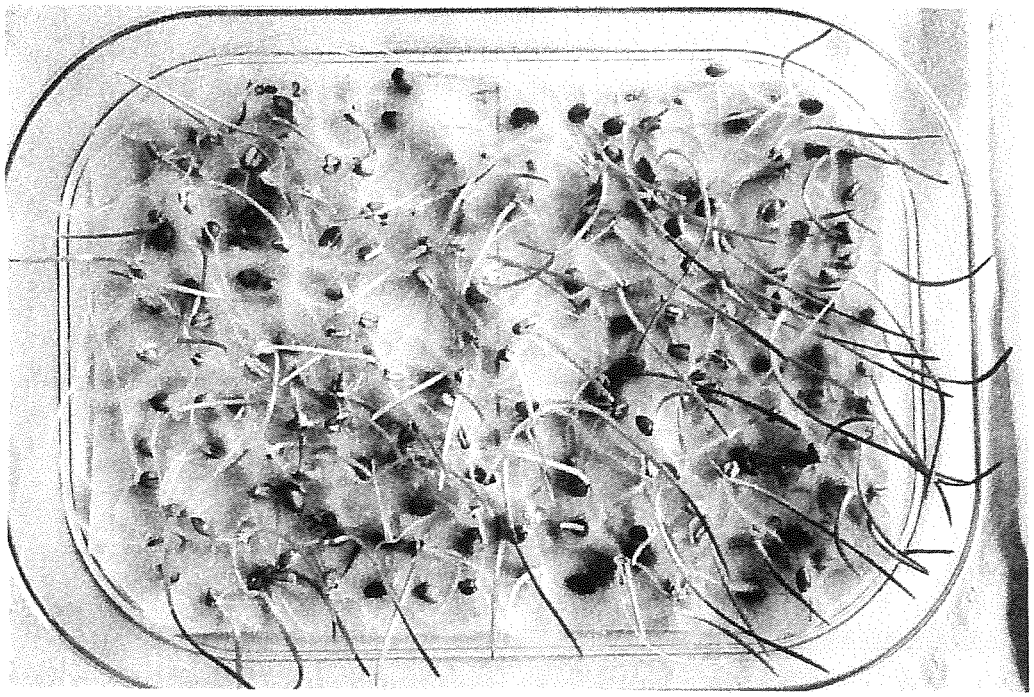
FIG. 2 is an image showing two test areas of Tartaros wheat seed naturally infected with fungus, wherein the two areas contain a formulation of thiram of different concentrations, wherein the left area the concentration is 3360 ppm and in the right area it is 840 ppm.

The effectivity of compositions of the invention were compared to those of antifungal compositions comprising thiram. The results obtained with "plant seed essay #1" are visualized in FIGS. 1 and 2, each containing a photograph comprising two test areas (left and right) of Tartaros wheat seed (harvest of 2014) naturally infected with fungus (predominantly *Fusarium*). All areas record the situation after seven days of sowing. The left area of FIG. 1 contains untreated seed, while the right area contains the natamycin composition of entry 5.5 of Table 5, which is present in a concentration of 400 ppm on the seed and has an antifungal effectivity of 4. The two areas in FIG. 2 contain a formulation of thiram of different concentration. In the left area the concentration is 3360 ppm, in the right area it is 840 ppm. In both areas, fungus growth is inhibited, the extent of which correspond to an effectivity of 3 on the indicated scale of 1-5 (standard effectivity). However, this is to a smaller extent than the inhibition by the natamycin composition of FIG. 1 (effectivity of 4). Moreover, it can clearly be seen that thiram has an phytotoxic effect as compared to natamycin, since the germination of the seeds in FIG. 2 is substantially less developed. The effect is the largest with the highest concentration of thiram (left area of FIG. 2). It can thus be concluded that natamycin compositions of the invention are more effective and less phytotoxic than known compositions such as thiram compositions.

It was further shown that natamycin compositions are highly stable when stored in the dark at room temperature, since no decrease in effectivity has been observed for compositions of more than one year old.

What is claimed is:

1. A process for preparing a composition comprising a bioactive molecule comprising the steps of:
    a) dissolving a bioactive molecule having at least one acid group with an aqueous base at pH≥11 to obtain a solution A; and
    b) neutralizing the solution A with an acid to obtain the composition comprising the bioactive molecule having a pH between 6 and 9,
    wherein polyethylene glycol (PEG) is added at a temperature between 30° C. and 60° C. before the neutralizing step,
    wherein the bioactive molecule is natamycin,
    wherein the base is an organic base chosen from the group consisting of choline hydroxide, choline chloride, choline bitartrate, choline monohydrogen-tartrate, choline-dihydrogen-citrate, branched polyethyleneimine, tetramethylammonium hydroxide, tetraethylammonium hydroxide, and tetrabutylammonium hydroxide,
    wherein the composition is an aqueous solution,
    wherein the natamycin is present in a range between 3 and 18 wt. %, relative to the total weight of the neutralized composition, and
    wherein the acid is selected from the group consisting of formic acid, acetic acid, propionic acid, sorbic acid, benzoic acid, malic acid, butanoic acid, hexanoic acid, hydroxybutanedioic acid, fumaric acid, tartaric acid, ascorbic acid, octanoic acid and nicotinic acid,
    wherein the amount of organic base ranges from 4-30 wt. % relative to the total weight of the composition,
    wherein the PEG is present in an amount from 30-90 wt. % based on the total weight of the composition,
    wherein the natamycin is stable in the aqueous solution as evidenced by lack of crystallization after 24 hours.

2. The process according to claim 1, wherein the neutralized composition contains natamycin between 4-10 wt. %.

3. The process according to claim 1, wherein the amount of organic base ranges from 4-30 wt. % relative to the total weight of the composition.

4. The process according to claim 1, wherein the organic base is choline hydroxide, and wherein a weight ratio between natamycin and choline hydroxide ranges between 1:0.4 and between 1:10.

5. The process according to claim 1, wherein 20-80 wt. % PEG having a molecular weight between 200 and 1000 daltons is added.

6. The process according to claim 1, wherein a weight ratio between natamycin and water is between 1:0.55 and 1:10, and wherein the amount of the organic base ranges between 10 and 25 wt. % relative to the total weight of the composition.

7. The process according to claim 1, wherein the weight % of natamycin is between 4 and 10 wt. %, wherein a weight ratio between natamycin and water is between 1:0.6 and 1:9, and wherein the amount of the organic base ranges between 10 and 25 wt. % relative to the total weight of the composition.

8. The process according to claim 1, wherein the organic base is choline hydroxide, and wherein a weight ratio between natamycin and choline hydroxide ranges between 1:0.45 and 1:10.

9. A process for preparing a composition comprising a natamycin comprising the steps of:
    a) dissolving the natamycin with an aqueous base at OW 1 to obtain a solution A including an ionic complex of the natamycin and the base,
    wherein the base is one or more of potassium hydroxide and sodium hydroxide,
    b) heating PEG to a temperature between 30° C. and 60° C.;
    c) adding the heated PEG to solution A and mixing therewith to form Solution A', and;
    d) neutralizing the solution A' with an acid to obtain the composition comprising the natamycin having a pH between 6 and 9,
    wherein the acid is one or more of formic acid, acetic acid, propionic acid, sorbic acid, benzoic acid, lactic acid, malic acid, butanoic acid, hexanoic acid, hydroxybutanedioic acid, citric acid, fumaric acid, tartaric acid, ascorbic acid, octanoic acid and nicotinic acid;
    wherein the natamycin is present in an amount from 3-18 wt. % based on the total weight of the composition,
    wherein the base is present in an amount from 4-30 wt. % based on the total weight of the composition,
    wherein the PEG is present in an amount from 30-90 wt. % based on the total weight of the composition,
    wherein the composition is an aqueous solution, and
    wherein the natamycin is stable in the aqueous solution as evidenced by lack of crystallization after 24 hours.

10. The process according to claim 9, wherein the solution A consists of the water, the base and the natamycin.

11. The process according to claim 9, wherein the PEG has a number average molecular weight of 200.

12. The process according to claim 9, wherein the acid is one or more of acetic acid and propionic acid.

13. The process according to claim 12, wherein the natamycin is present in an amount from 4 to 12 wt. % based on the total weight of the composition.

14. The process according to claim 13, wherein the base is present in an amount from 7 to 25 wt. % based on the total weight of the composition.

15. The process according to claim 14, wherein PEG is present in an amount from 30 to 80 wt. % based on the total weight of the composition.

* * * * *

UNITED STATES PATENT AND TRADEMARK OFFICE
CERTIFICATE OF CORRECTION

PATENT NO.          : 11,839,217 B2
APPLICATION NO.     : 16/337606
DATED               : December 12, 2023
INVENTOR(S)         : Wilhelmus Antonius Maria Van Lith It is certified that error appears in the above-identified patent and that said Letters Patent is hereby corrected as shown below:

In the Claims

In Claim 9, Column 22, Line 16, delete "OW" and insert -- $pH \geq 11$ --.

Signed and Sealed this
Twentieth Day of February, 2024

Katherine Kelly Vidal
*Director of the United States Patent and Trademark Office*